United States Patent [19]

Hutchinson et al.

[11] Patent Number: 5,817,323
[45] Date of Patent: Oct. 6, 1998

[54] SOFT GELATIN CAPSULE SHELL COMPOSITIONS

[75] Inventors: Keith Graeme Hutchinson, Gloucestershire; Kelvin Royce Garnett, Wiltshire, both of Great Britain; Gerhard Fischer, Eberbach, Germany; Nicola Sandra Page, Wiltshire, Great Britain

[73] Assignee: R.P. Scherer Corporation, Troy, Mich.

[21] Appl. No.: 454,102

[22] PCT Filed: Jun. 23, 1994

[86] PCT No.: PCT/GB94/01361

§ 371 Date: Mar. 26, 1996

§ 102(e) Date: Mar. 26, 1996

[87] PCT Pub. No.: WO95/00123

PCT Pub. Date: Jan. 5, 1995

[30] Foreign Application Priority Data

Jun. 28, 1993 [GB] United Kingdom ................ 9313329.6

[51] Int. Cl.⁶ ................ A61K 9/20; A61K 9/48

[52] U.S. Cl. .................. 424/439; 424/441; 424/451; 424/484; 424/488; 514/774; 514/777; 514/778

[58] Field of Search ................ 424/439, 451, 424/456, 455, 441, 484, 488

[56] References Cited

U.S. PATENT DOCUMENTS 4,935,243   6/1990   Borkan et al. .................. 424/441

*Primary Examiner*—Thurman K. Page
*Assistant Examiner*—James M. Spear
*Attorney, Agent, or Firm*—Wallenstein & Wagner, Ltd.

[57] ABSTRACT

A composition for use in the shell of a comestible capsule comprising Gelatin and a plasticiser such as Glycerol together with a further component which forms a secondary matrix for the plasticiser. The provision of this secondary matrix enables the relative amount of the gelatin to the plasticiser to be reduced which shortens disintegration time in the mouth. The further component is typically unbleached potato starch acetate.

20 Claims, No Drawings

SOFT GELATIN CAPSULE SHELL COMPOSITIONS

This application is a 371 of PCT/GB94/01361 filed Jun. 23, 1994.

This invention relates to compositions for the use in comestible and other soft gelatin capsules, of the type used in oral drug delivery systems and in food products and food additives.

It is known to encapsulate medicinal and food products using capsule material which is itself comestible. The shell material for such capsules is normally gelatin based, and as a consequence largely void of flavour, odour and colour. While such capsules have been used with great success, gelatin based shell materials can be relatively slow in disintegrating, and particularly where an encapsulated product for oral use is intended to be released in the mouth, faster disintegration rates are desirable.

Examples of gelatin based capsules are described in the following Patent Specifications to which reference is directed:

EP-A-0 233 231 & U.S. Pat. No. -A-4,804,542

EP-A-0 199 034

EP-A-0 120 248 & U.S. Pat. No. -A-4,744,988

U.S. Pat. No. -A-2 580 863

Shell materials of the above type normally comprise Gelatin and a physiologically acceptable plasticiser such as Glycerol, the Gelatin forming a matrix for the plasticiser. The relative quantities of these components is important to ensure reliable encapsulation, and storage characteristics. However, we have found that the amount of Gelatin can be reduced if a further component is included which forms a secondary matrix for the plasticiser. According to the invention therefore, a composition for use in the shell of a capsule comprises Gelatin and a plasticiser, the Gelatin forming a primary matrix for the plasticiser; and a further component compatible with the Gelatin, which component forms a secondary matrix for the plasticiser. Typically, the composition includes 18 to 30% by weight of Gelatin and 30 to 45% by weight of the plasticiser. The further component is normally a potato starch acetate, another starch derivative, starch itself or mixtures thereof.

The invention also provides chewable compositions formulated according to the above criteria, and comestible capsules with shells comprising such compositions. Additionally disclosed herein is a process for the preparation of a composition according to the invention comprising the steps of mixing the further component with water and the plasticiser; adding the gelatin to the mixture; allowing the mixture to crumb; heating the mixture; leaving the heated mass to stand; and deaerating the mass with minimum water loss.

In preferred compositions according to the invention the amount of the further component does not exceed 25%, and is normally no more than 12% by weight. The preferred further component is unbleached starch acetate, most preferably derived from potato, and a suitable product is available under the Trade Name PERFECTAMYL GEL MB from Avebe BA. Another suitable potato starch acetate is available from Roquette Freres, under the Trade Name CLEARAM.

A typical amount of the further component is up to 12% by weight. While higher levels result in a more chewable product, solubility is likely to deteriorate. Additionally, examination of capsules formed from selected compositions using higher levels of starch acetate as the further component, showed that some starch aggregation was taking place. A preferred maximum level is 10%; 8% is particularly preferred.

The quantities of gelatin specified above are substantially less than is normally used in known gelatin based capsule shell compositions. Similarly, the amount of plasticiser is relatively increased. This is made possible by the presence of the further component which reduces the effect of the plasticiser on the gelatin which might otherwise result in a composition which does not form a structure of strength sufficient for encapsulation and storage. In effect, the further component forms a secondary compatible matrix, typically in the range 20° to 60° C., for the plasticiser within the primary gelatin matrix which does not adversely effect the function of the plasticiser, but reduces its tendency to form an adherent surface on the eventual product. It will be appreciated that a certain quantity of the further component is always required in the composition, and a typical minimum level would be 3% by weight.

The plasticiser is usually Glycerol, but suitable alternatives are Xylitol, Sorbitol, Polyglycerol, non-crystalising solutions of Sorbitol, glucose, fructrose and glucose syrups with different equivalents. One preferred alternative is ANIDRISORB (a proprietary mixture of Sorbitol, Sorbitans, Maltitol and Mannitol, available from Roquette Freres). These may be used alone or in combination. In a combination of plasticisers including Glycerol, the Glycerol typically comprises at least 30% by weight of the combination, normally in the range 30% to 70% by weight. The inclusion of Glycerol provides a more 'chewable' product. Using an alternative plasticiser or plasticiser component produces a less 'chewable' product, but one which does disintegrate more quickly than known formulations.

The chewability of compositions according to the invention can be enhanced by the inclusion of an oil such as fractionated coconut oil. Up to 15%, preferably no more than 10%, can be included in the composition, but at high levels, the resultant product appears cloudy. A preferred quantity is around 3% to 7%, typically 5% by weight. Oil disperses within the shell structure as microscopic droplets. These prevent some of the gelatin bonds forming, and hence act in a similar way to the plasticiser. However, the plasticiser can allow a formation of hydrogen bonds across the interstitial spaces of the gel matrix and some of the liquid in the spaces is removed as the gel dries. As a result more gelatin links form, stiffening the matrix. The oil inhibits the formation of these additional gelatin links resulting in a more chewable product, although the pressure exerted by the gelatin causes some droplets to coalesce.

Preferred embodiments of the invention also include a bleached starch acetate, normally derived from potato, and typically in an amount up to 12% by weight, preferably 6% to 10%. A suitable such potato starch derivative is also available from Avebe BA under the Trade Name PERFECTAMYL GEL 45. This starch derivative is soluble in the manufacture of compositions according to the invention, and therefore remains in solution until the composition dries. At this stage the bleached starch acetate forms a film, thus acting as a bulking agent. It causes a degree of stickiness in the composition as it sets, which is counteracted by the setting of the gelatin and the preferred further component; unbleached starch acetate. A combination of both starches was found to replace higher levels of gelatin than the unbleached acetate alone. Similar effects can be achieved by using a variety of soluble materials.

Capsules may be formed using compositions according to the invention by any suitable technique. Two such techniques are the concentric cylinder and the rotary dye methods. The latter has been used for many years by R. P. Scherer Corporation and its associated companies, and is described in the Sep. 1985 edition of Pharmaceutical Technology, to which reference is directed. Briefly, the composition in a liquid state is spread on a suitably prepared and cooled drum upon which the gel mass sets to a non-sticky film. Where two similar films merge on encapsulation, seals are formed which become stronger as the mass dries. The further component makes a significant contribution to film strength at this stage, and in this respect its selection is important. The preferred component is potato starch acetate which adds structure to the gel matrix by the association of starch molecules to form a starch gel inside the gelatin matrix.

The use of bleached starch in addition to the unbleached starch results in improved suitability for chewing because the starches swell at a different rate to gelatin without substantial cross-bonding. Consequently, they are readily separable on chewing.

Compositions embodying the invention and a known composition, will now be described by way of example. Details of the compositions are as follows. Formulations used in which the plasticiser is Glycerol

| Material | Formulation Number | | | | | |
|---|---|---|---|---|---|---|
| % by weight | 1 | 2 | 3 | 4 | 5 | 6 |
| Gelatin | 26 | 26 | 24 | 28 | 26 | 38.4 |
| Glycerol | 35 | 35 | 40 | 39 | 36 | 29.2 |
| Water | 27 | 22 | 20 | 25 | 22 | 32.4 |
| Potato Starch Acetate | 12 | 10 | 6 | 3 | 6 | — |
| Bleached Potato Starch Acetate | — | 7 | 10 | — | 10 | — |
| Oil | — | — | — | 5 | — | — |

EXAMPLE S1 (USING FORMULATION 1)

A gelatin decoction was prepared by blending the Potato Starch Acetate with the water and glycerol to form a slurry. After addition of the gelatin with stirring, and allowing the mixture to 'crumb' under vacuum for ten minutes, the decoction was prepared in a per se known manner using a waterbath with circulator in which to heat the vessel containing the mixture to 90° C. and leaving to stand for 35 minutes. The gel mass is then deaerated using a vacuum pump while minimising water loss.

Capsules were readily made with a flavoured placebo paste formulation for fill, which were easily chewable.

EXAMPLE S2 (USING FORMULATION 2)

A gelatin decoction was prepared by blending both starch derivatives with the water and glycerol to form a slurry. After addition of the gelatin, the decoction was prepared in a per se known manner.

Capsules were readily made with a flavoured placebo paste formulation for fill, which were very easily chewable.

EXAMPLE S3 (USING FORMULATION 3)

A gelatin decoction was prepared as described in example S2. To this was added colours and flavours totalling 6.0% of the gelatin mass using a high speed blender.

Capsules were readily made with a flavoured placebo formulation for fill. These capsules were very easily chewable.

EXAMPLE S4 (USING FORMULATION 3)

The gelatin decoction described was blended to colour and flavour and used to make capsules with an oil fill material. Disintegration testing in distilled water at 70° C. gave results of capsule rupture and full shell disintegration approximately 40–50% faster for the capsules using the invention than the known shell formulation (6).

EXAMPLE S5 (USING FORMULATION 4)

A gelatin decoction was prepared as described in example S2 with the component of formulation 4 excluding the oil. To this decoction was added colours and flavours identical to example S3 and vegetable oil 3% (flavour oil level was 2% making a total oil content of 5%).

Capsules were readily made with a flavoured placebo paste fill which were soft and easily chewable.

EXAMPLES S6, S7 AND S8 (USING FORMULATION 5)

Gelatin decoctions were prepared as described in example S2.

These were blended to different colours and flavours with a range of additions of 3–7.2% of the gelatin decoction used.

Capsules with flavoured paste fills containing active vitamin compositions were readily made. All were easily chewable with a very notable improvement compared to the same recipes using formulation 6 as the base shell formulation.

EXAMPLE S9 (USING FORMULATION 5)

A gelatin decoction was prepared in two stages. First, the Potato Starch derivatives were blended with 1½ times their own weight of glycerol from the formulation. This slurry was heated to 50°–60° C. and added to a gelatin decoction made from all remaining materials in a per se known manner. The mixture was stirred on a high speed blender until a temperature of 60°–65° C. was attained. This mixture was then further blended with colours and flavours totalling 6.25% of the mixture weight.

Capsules with flavoured paste fill containing active vitamin components were readily made and were identical in chewability to the same formulation of capsules made in Example S7.

EXAMPLE S10 (PRIOR ART, USING FORMULATION 6)

A standard shell was prepared in a per se known manner and blended to the same colour and flavour and used to make capsules with the same fill formulation. These capsules had a very tough chewing characteristic requiring approximately twice the time (60–65 secs) to chew before swallowing. A slippery, slimy mouth feel was also noted for these capsules. Formulations used including alternative plasticisers

| Material | Formulation Number | | | | |
|---|---|---|---|---|---|
| % by weiqht | 7 | 8 | 9 | 10 | 11 |
| Gelatin 195 Bloom Acid processed | 25 | | 25 | 25 | 25 |
| Gelatin Succinated | | 34 | | | |
| Glycerol | 24 | 20 | 24 | 12 | |
| Sorbitol 70% | 12 | 10 | | 24 | |
| Anidrisorb 85/70 | | | 12 | | |
| Polyglycerol | | | | | 36 |
| Purified Water | 23 | 29 | 23 | 23 | |
| Potato Starch Acetate | 6 | 3 | 6 | 6 | 6 |
| Bleached Potato Starch Acetate | 10 | 4 | 10 | 10 | 10 |

EXAMPLES S11 to S14

Gelatin decoctions were prepared using formulations 7 to 11, by first blending the starch derivatives with the water and plasticiser components (Glycerol, Sorbitol, Andrisorb, Polyglycerol) to form a slurry, to which the Gelatin was added as in Example S2. Capsules made according to these examples exhibit short disintegration times on contact with water, but are less readily chewable than those made according to Examples S1 to S9.

From experimental work conducted using the above examples it appears that any plasticiser normally used in soft gelatin capsules can be used in compositions embodying this invention. The matrix formed by the lower Gelatin content, modified starch components, and high plasticiser contact give faster disintegration times than those exhibited by known formulations, although improvement in chewability was clearly most apparent in the formulations which used Glycerol as the plasticiser and/or an oil.

As will be apparent from Examples S1 to S10 above, the material in capsules of the present invention of the wall can itself contain significant components contributing to its overall properties. This is of particular value where two component elements are to be kept separate prior to use and they may, of course, be kept separate between the capsule material and the encapsulated product.

Products provided in liquid form for encapsulation in capsules of the invention typically incorporate hydrophobic or hydrophilic carrier media or a combination of both. Examples of hydrophilic solvents or carrier media include: Polyethylene Glycols (PEGs), particularly PEG 400 and PEG 600; Glycofurol; Polyglycerols; propylene Glycol; Ethanol; Water; Glycerol; transcutol, polysorbate and propylene carbonate.

Hydrophobic solvent/carrier media also include hydrogenated natural oils, synthetic oils such as polymethylsiloxane (dimethicone), neutral oils such as fractionated coconut oil, mineral oils, triacetin, ethyl oleate, and other natural oils such as: Soyabean Oil; Arachis oil; Corn Oil; Sesame Oil; Olive Oil; Rapeseed Oil; Sunflower Oil and Safflower Oil. Thickened fill products with high viscosities are preferred as they disperse less rapidly and improve palatability. They also reduce the contrast between the shell and the fill materials.

Capsules embodying the invention can include flavouring and aromatic components, in either the encapsulated contents, or in the capsule shell material itself. Suitable components include essential oils such as lemon, orange and peppermint oils; fruit flavours; aniseed; liquorice; caramel; honey; cream; various spices and combinations of these and other flavours. Such components are available from International Flavours & Fragrances, IFF (GB) Ltd. of Haverhill, Suffolk, CB9 8LG ENGLAND. Natural or artificial sweeteners can also be used, such as:

Aspartame, Saccharin, Acesulphame K, Neohesperidine hydrochloride, Mannitol, Xylitol, and Maltitol;

taste-masking ingredients such as sodium bicarbonate, ion exchange resins, cyclodextrins and adsorbates;

suspending agents such as beeswax, hydrogenated vegetable oils, glycerol monostearate or glycerol palmitate, and high molecular weight PEGs; e.g.1500 to 6000.

Where the encapsulated contents include particles in suspension, the particles may be separately coated, typically with suitably sweetened or flavoured coatings, such as those referred to above. Such a coating can serve as either or both of a taste-masking agent and a stabiliser in the suspension.

By way of further illustration some contents formulations will be given by way of example.

Example C1

| | |
|---|---|
| Fractionated Coconut Oil BP/Ph Eur | 75% |
| Gelucire 42/12* | 7% |
| Span 20** | 3% |
| Mannitol BP | 9% |
| Aspartame US NF XVII | 1% |
| Flavour | 5% |
| | 100% |

*Glycerides and polyglycides of fatty acids of vegetable origin.
**Sorbitan fatty acid esters (BP 1980)

Example C2

| | |
|---|---|
| Imwitor 742* | 80% |
| Tween 80** | 14% |
| Aspartame US NF XVII | 1% |
| Flavour | 5% |
| | 100% |

*Caprylic/Capric mono-di & tri-glycerides (Medium chain partial glycerides US NF XVII)
**Polysorbate 80 BP Example C3

| | |
|---|---|
| Polyethylene Glycol 400 BP | 56% |
| Glycerol BP | 8% |
| Water, Purified BP | 5% |
| Mannitol BP | 25% |
| Aspartame US NF XVII | 1% |
| Flavour | 5% |
| | 100% |

Example C4

| | |
|---|---|
| Lycasin 80/55* | 88.5% |
| Aerosil 200** | 1.5% |
| Glycerol BP | 5% |
| Flavour | 5% |
| | 100% |

*Hydrogenated Glucose Syrup
**Colloidal Silicon Dioxide

Example C5

| | |
|---|---|
| Fractionated Coconut Oil BP | 58% |
| Tween 80* | 25% |
| Mannitol BP | 10% |
| Sodium Saccharin BP | 2% |
| Flavour | 5% |
| | 100% |

*Polysorbate 80 BP

Example C6

| | |
|---|---|
| Fractionated Coconut Oil BP | 95% |
| Flavour | 5% |
| | 100% |

Example C7

| | |
|---|---|
| Fractionated Coconut Oil BP/Ph Eur | 75% |
| Gelucire 42/12 | 7% |
| Span 20 | 3% |
| Mannitol BP | 9% |
| Peppermint Oil BP | 6% |
| | 100% |

Example C8

| | |
|---|---|
| Fractionated Coconut Oil BP/Ph Eur | 75% |
| Gelucire 42/12 | 7% |
| Span 20 | 3% |
| Mannitol BP | 9% |
| Aspartame US NF XVII | 1% |
| Peppermint Oil BP | 5% |
| | 100% |

-continued

Example C9

| | |
|---|---|
| Polyethylene Glycol 400 BP | 53.3% |
| Glycerol BP | 7.6% |
| Water Purified BP | 4.8% |
| Paracetamol BP | 28.6% |
| Aspartame US NF XVII | 1.0% |
| Lemon Flavour 17.42.7201 | 4.8% |
| | 100% |

Example C10

| | |
|---|---|
| Polyethylene Glycol 400 BP | 53.3% |
| Glycerol BP | 7.6% |
| Water Purified BP | 4.8% |
| Paracetamol BP | 28.6% |
| Saccharin, Sodium BP | 1.0% |
| Lemon Flavour 17.42.7201 | 4.8% |
| | 100% |

We claim:

1. A composition for use in the shell of a capsule comprising Gelatin and a plasticiser, the Gelatin forming a primary matrix for the plasticiser; and a starch acetate compatible with the Gelatin, which starch acetate forms a secondary matrix for the plasticiser.

2. A composition according to claim 1 including 18 to 30% by weight of Gelatin and 30 to 45% by weight of the plasticiser.

3. A composition according to claim 1 wherein the plasticiser is selected from Glycerol, Xylitol, Sorbitol, Polyglycerol, non-crystalising solutions of Sorbitol, glucose, fructose, glucose syrup, and combinations thereof.

4. A composition according to claim 3 wherein the plasticiser is Glycerol.

5. A composition according to claim 1 wherein a mixture of starch and starch acetate forms the secondary matrix.

6. A composition according to claim 1 wherein the starch acetate is unbleached.

7. A composition according to claim 6 wherein the unbleached starch acetate is unbleached potato starch acetate.

8. A composition according to claim 1 including up to 12% by weight of the starch acetate.

9. A composition according to claim 8 wherein the amount of the starch acetate is in the range 3 to 10% by weight.

10. A composition according to claim 1 including up to 10% by weight of oil.

11. A composition according to claim 10 wherein the oil is fractionated coconut oil.

12. A composition according to claim 9 including up to 12% bleached starch acetate.

13. A composition according to claim 12 wherein the bleached starch acetate is derived from potato.

14. A chewable composition according to claim 12.

15. A comestible capsule with a shell comprising a composition according to claim 12.

16. A process for the preparation of a composition according to claim 1 comprising the steps of mixing the starch acetate with water and the plasticiser; adding the gelatin to the mixture; allowing the mixture to crumb; heating the mixture; leaving the heated mass to stand; and deaerating the mass with minimum water loss.

17. A process according to claim 16 wherein the starch acetate is unbleached.

18. A composition according to claim 2 wherein the plasticizer is selected from Glycerol, Xylitol, Sorbitol, Polyglycerol, non-crystallizing solutions of Sorbitol, glucose, fructose, glucose syrup, and combinations thereof.

19. A composition for use in the shell of a capsule comprising:

a plasticiser;

a Gelatin forming a primary matrix for the plasticiser;

a further component compatible with the Gelatin and forming a secondary matrix for the plasticiser; and, wherein the composition contains up to 10% by weight of oil.

20. The composition of claim 19 wherein the oil is fractionated coconut oil.

* * * * *